United States Patent
Murugesan et al.

(10) Patent No.: US 9,828,060 B2
(45) Date of Patent: Nov. 28, 2017

(54) AUTOMATED E-ASSIST ADJUSTMENT TO PREVENT USER PERSPIRATION

(71) Applicant: GM Global Technology Operations LLC, Detroit, MI (US)

(72) Inventors: Prakash Murugesan, Toronto (CA); Norman J. Weigert, Whitby (CA); Mark A. Manickaraj, Scarborough (CA); Jarvis Chau, Markham (CA)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 2 days.

(21) Appl. No.: 14/881,281

(22) Filed: Oct. 13, 2015

(65) Prior Publication Data

US 2017/0101158 A1    Apr. 13, 2017

(51) Int. Cl.
| | | |
|---|---|---|
| B62M 6/50 | (2010.01) | |
| A61B 5/00 | (2006.01) | |
| B60W 40/08 | (2012.01) | |
| B60W 50/10 | (2012.01) | |
| A61B 5/024 | (2006.01) | |

(52) U.S. Cl.
CPC ............ *B62M 6/50* (2013.01); *A61B 5/4266* (2013.01); *A61B 5/6895* (2013.01); *B60W 40/08* (2013.01); *B60W 50/10* (2013.01); *A61B 5/024* (2013.01); *A61B 5/4875* (2013.01); *B60W 2040/0872* (2013.01); *B62K 2204/00* (2013.01); *B62K 2207/00* (2013.01)

(58) Field of Classification Search
CPC ........ B62M 6/50; B60W 50/10; B60W 40/08; B60W 2040/0872; B62K 2207/00; B62K 2204/00; A63B 2220/80–2220/89
See application file for complete search history.

(56) References Cited

U.S. PATENT DOCUMENTS

| | | | | |
|---|---|---|---|---|
| 2007/0123390 A1* | 5/2007 | Mathis | ............... | A63B 24/0084 482/8 |
| 2008/0071436 A1* | 3/2008 | Dube | ....................... | B62M 6/45 701/22 |
| 2011/0254673 A1* | 10/2011 | Jean | ......................... | B62M 6/45 340/432 |
| 2013/0138281 A1* | 5/2013 | Chien | ...................... | B62M 6/50 701/22 |
| 2013/0173413 A1* | 7/2013 | Page | .................. | G06Q 30/0621 705/26.5 |
| 2014/0229046 A1* | 8/2014 | Gros | ........................ | B62J 99/00 701/22 |
| 2014/0275854 A1* | 9/2014 | Venkatraman | ......... | A61B 5/721 600/301 |
| 2015/0019062 A1* | 1/2015 | Previdi | ..................... | B60L 7/12 701/22 |
| 2015/0081056 A1* | 3/2015 | Yeh | ..................... | G06F 19/3406 700/91 |
| 2016/0220808 A1* | 8/2016 | Hyde | .................... | A61N 1/0452 |
| 2016/0304157 A1* | 10/2016 | Craven | .................... | B62M 6/50 |
| 2016/0375308 A1* | 12/2016 | Anderson | .......... | A63B 24/0087 482/5 |

* cited by examiner

*Primary Examiner* — Rami Khatib
*Assistant Examiner* — Jeffrey Boomer
(74) *Attorney, Agent, or Firm* — Lorenz & Kopf, LLP

(57) ABSTRACT

A method may include determining whether a sweat sensor is available. E-assist may be provided when a sweat sensor is not available by determining a sweat threshold and determining whether the sweat threshold is surpassed. When a sweat sensor is available, e-assist may be provided when the sweat sensor senses sweat.

17 Claims, 2 Drawing Sheets

AUTOMATED E-ASSIST ADJUSTMENT TO PREVENT USER PERSPIRATION

TECHNICAL FIELD

The field to which the disclosure generally relates includes electric cycles, and more particularly, includes automated e-assist adjustment in electric cycles.

BACKGROUND

An electric cycle may have various wheel arrangements and may include an on-board electric motor that can be used for propulsion of the cycle through one or more gears.

SUMMARY OF ILLUSTRATIVE VARIATIONS

A number of variations may involve a method that may include determining whether a sweat sensor is available. E-assist may be provided when a sweat sensor is not available by determining a sweat threshold and determining whether the sweat threshold is surpassed.

A number of other variations may involve a method of providing e-assist to propel a cycle and may include determining whether a sweat sensor is available. When a sweat sensor is available, the method may include at least one of: a. determining a sweat threshold, and determining whether the sweat threshold is surpassed, or b. determining whether the sweat sensor senses sweat.

A number of additional variations may involve a system providing e-assist to propel a cycle and may include a crank that may propel the cycle with rider effort. A motor may be connected to the cycle and may providing e-assist to propel the cycle. A controller may communicate with the motor, and an input device may provide rider input to the controller.

Other illustrative variations within the scope of the invention will become apparent from the detailed description provided herein. It should be understood that the detailed description and specific examples, while disclosing variations within the scope of the invention, are intended for purposes of illustration only and are not intended to limit the scope of the invention.

BRIEF DESCRIPTION OF THE DRAWINGS

Select examples of variations within the scope of the invention will become more fully understood from the detailed description and the accompanying drawings, wherein.

DETAILED DESCRIPTION OF ILLUSTRATIVE VARIATIONS

The following description of the variations is merely illustrative in nature and is in no way intended to limit the scope of the invention, its application, or uses.

Figure 1:
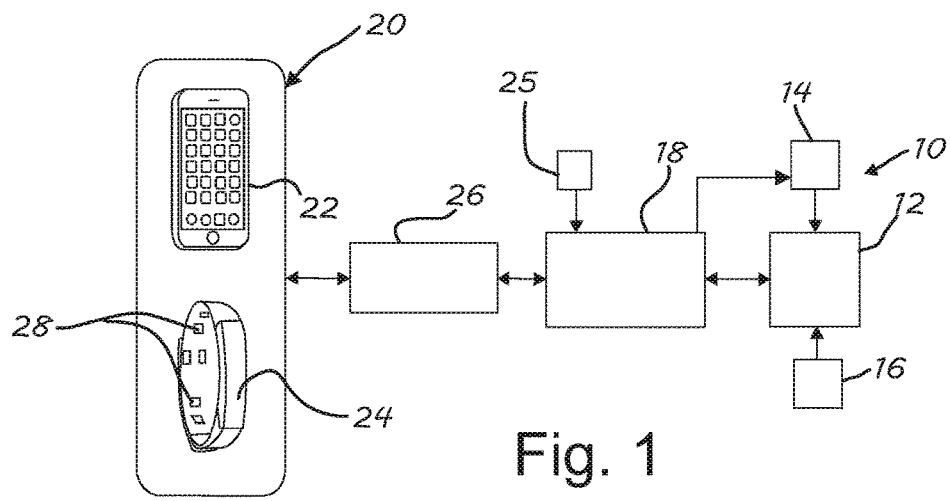
FIG. 1 illustrates a block diagram of an automated e-assist system according to a number of variations.

FIG. 1 illustrates a number of variations which may include an automated e-assist system 10. The automated e-assist system 10 may be associated with a cycle 12 that may be propelled by a pedaling rider through a crank 16. The cycle 12 may be propelled by a motor 14 that may be used to assist the rider as a supplement, or alternative, to input through the crank 16. In a number of variations the cycle 12 may be propelled solely by the motor 14 without pedaling effort by the rider at the crank 16. The automated e-assist system 10 may be used to limit the level of rider exertion and may be used to avoid rider perspiration, which may be desirable in uses of the cycle 12, such as for a commuting vehicle.

In a number of variations the motor 14 may receive input from a controller 18 that may be onboard the cycle 12. Methods, algorithms, or parts thereof may be implemented in a computer program product of the controller 18 including instructions or calculations carried on a computer readable medium for use by one or more processors to implement one or more of the method steps or instructions. The computer program product may include one or more software programs comprised of program instructions in source code, object code, executable code or other formats; one or more firmware programs; or hardware description language (HDL) files; and any program related data. The data may include data structures, look-up tables, or data in any other suitable format. The program instructions may include program modules, routines, programs, objects, components, and/or the like. The computer program may be executed on one processor or on multiple processors in communication with one another.

In a number of variations, the program(s) may be embodied on computer readable media, which can include one or more storage devices, articles of manufacture, or the like. Illustrative computer readable media may include computer system memory, e.g. RAM (random access memory), ROM (read only memory); semiconductor memory, e.g. EPROM (erasable, programmable ROM), EEPROM (electrically erasable, programmable ROM), flash memory; magnetic or optical disks or tapes; and/or the like. The computer readable medium also may include computer to computer connections, for example, when data may be transferred or provided over a network or another communications connection (either wired, wireless, or a combination thereof). Any combination(s) of the above examples is also included within the scope of the computer-readable media. It is therefore to be understood that methods may be at least partially performed by any electronic articles and/or devices capable of executing instructions corresponding to one or more steps of the disclosed methods.

In a number of variations the controller 18 may be linked to one or more input devices 20. The input devices 20 may, as examples, include a computing device such as a smartphone device 22, or a selector device such as input wristband 24. Other input devices 20 may be any device that can communicate information to the controller 18, including but not limited to, a manual selector onboard the cycle 12, a tablet, a personal computer or other internet connected device, or another device wirelessly connected to, or with a wired connection to, the cycle 12, including items such as a watch, smart glasses, or other wearable device. The input device or devices 20 may communicate with the controller 18 through an interface 26. The interface 26 may be wired or wireless. In the case of a wireless interface, the controller 18 may include a receiver, or a transmitter and receiver, for purposes of communication with the input device or devices 20. A number of sensors 25 may communicate with the controller 18. The sensors 25 may include any of a number of devices providing information such as ambient temperature, humidity, wind speed and direction, route slope, and rider status data such as hydration level, heart rate and sweat rate. In a number of variations one or more sensors may be incorporated in the input device or devices 20 such as a sweat sensor 28 in the input device 24, or in another input device. In a number of variations inputs such as ambient temperature may be provided by the smartphone 24 by accessing available information, such as from the internet. The controller 18 may be preprogrammed to operate the motor 14 to provide propulsion assistance (e-assist), according to set algorithms in the controller 18 and/or inputs received from the input device or devices 20, and/or the sensors 25.

Figure 2:
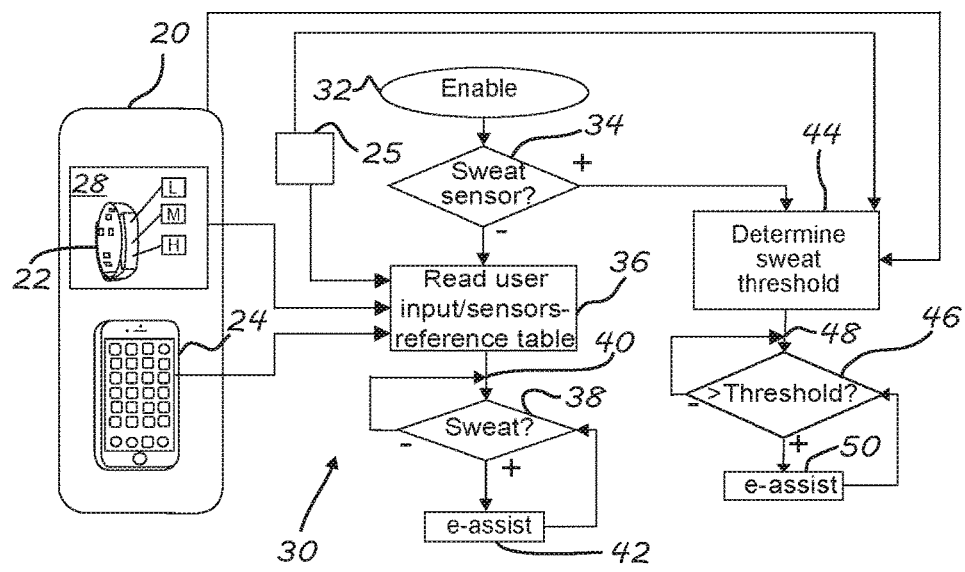
FIG. 2 illustrates an automated e-assist adjustment method according to a number of variations.

In a number of variations a method carried out, at least in part by the controller 18, is illustrated in FIG. 2 as method 30. The method 30 may control operation of the motor 14 to provide e-assist to the rider inputs at crank 16, to propel the cycle 12. E-assist may be provided to limit exertion or avoid perspiration of the rider by offsetting the need for rider pedal effort with torque supplied by the motor 14. Initiation of the method 30 may occur when an anti-perspiration mode is enabled at step 32. Enablement may be selected by the rider or may be triggered by the controller 18. From step 32 the method 30 may proceed to step 34 where a determination may be made as to whether a rider sweat sensor is available and actively communicating with the controller 18. For example the sensors 25 may be contained in a device that may be worn by the rider and that may sense the presence of moisture. Also for example, the sensor 25 may monitor and report conductivity levels or changes on the rider's skin. The sensors 25 may be located in the input device or devices 20 and may be the sweat sensor 28.

In a number of variations when it is determined at step 34 that a sweat sensor is not available, the method 30 may proceed to step 36. Step 36 may reference user input from the input device or devices 20. The user may provide a preferred operation exertion level setting, for example, low, medium, and high settings. A low level setting "L" may be selected when the rider prefers a low level of e-assist and a higher level of physical exertion. A medium "M" setting may be selected when the rider prefers a medium level of e-assist and exertion. A high "H" setting may be selected when the rider prefers a high level of e-assist and a low level of physical exertion. Step 36 may reference environmental data, such as from sensors 25 and/or the input device or devices 20. The environmental data may include ambient temperature, humidity, wind speed and direction, elevation, terrain information, route slope, speed, and rider status data such as hydration level, heart rate and sweat rate. Step 36 may use a lookup table that categorizes the numerical values of the environmental data for each of the user input settings to determine a threshold sweat level indicative of rider exertion under the existing conditions where e-assist is needed to avoid sweating. The rider may experience a learning curve through usage and may adjust the user input level. For example, if the cycle 12 is used for a daily commute, the rider may, through experience, learn the preferred setting for certain conditions and/or route segments.

In a number of variations the method 30 may proceed from step 36 to step 38 where a determination of whether passing the sweat threshold to the sweat zone is incipient or has occurred. If the determination at step 38 is negative, the method 30 may return to point 40 and step 38 may be repeated at a selected time interval. If the determination at step 38 is positive, the method 30 may proceed to step 42 where e-assist is initiated or increased if previously initiated, such as by supplying increased current to the motor 14. From step 42 the method 30 may return to step 38 where a new determination may be made of whether the sweat threshold is surpassed. Steps 38 and 42 may be repeated until the conditions fall below the sweat threshold, and the method 30 may return to point 40.

Returning to step 34, in a number of variations, if a positive determination is made that a sweat sensor is available, the method 30 may proceed to step 44. Step 44 may use information provided from the input device or devices 20, and from the sensors 25, including the sweat sensor 28. Environmental data from the sensors 25 may include ambient temperature, humidity, wind speed and direction, route slope, speed, and rider status data such as hydration level, heart rate and sweat rate. Step 44 may use a lookup table that categorizes the numerical values of the environmental data for each of the user input settings to determine a threshold sweat level indicative of rider exertion under the existing conditions where e-assist is needed to avoid sweating. The sweat sensor 28 may provide information on actual rider sweat conditions. The rider may experience a learning curve through usage and may adjust the user input level. For example, if the cycle 12 is used for a daily commute, the rider may, through experience, learn the preferred setting for certain conditions and/or route segments.

In a number of variations the method 30 may proceed from step 44 to step 46 where a determination of whether passing the sweat threshold is incipient or has occurred. If the determination at step 46 is negative, the method 30 may return to point 48 and step 46 may be repeated at a selected time interval. If the determination at step 46 is positive, the method 30 may proceed to step 50 where e-assist is initiated or increased if previously initiated, by supplying increased current to the motor 14. From step 50 the method 30 may return to step 46 where a new determination may be made of whether the sweat threshold is surpassed. Steps 46 and 50 may be repeated until the conditions fall below the sweat threshold, and the method 30 may return to point 48. At step 46, an input from the sweat sensor 28 that sweating is occurring leads to a positive determination regardless of the environmental data from the other sensors 25 and the input settings from the input device or devices 20. The sensed level of sweating may be used to determine the level of e-assist provided. The method 30 may learn from actual sweat data relative to environmental data and user settings to determine incipient sweating events and proactively provide e-assist to avoid sweat from occurring.

Figure 3:
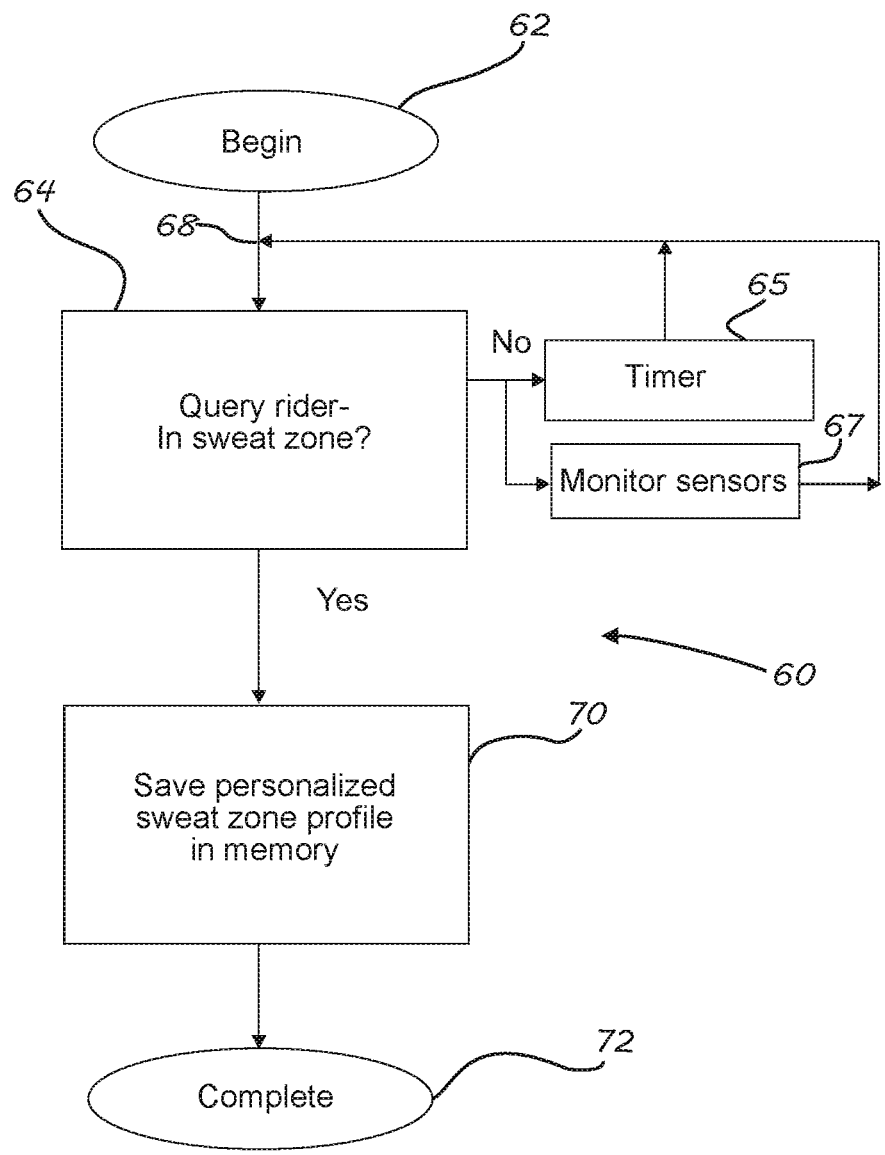
FIG. 3 illustrates learning steps for an automated e-assist adjustment method according to a number of variations.

When biometric sensors, such as sweat sensors are active, the method may use data received therefrom to make an intelligent decision on "if" the user is in, or nearing, the sweat zone. With reference to FIG. 3, to increase the intelligence level of the decision, the method 30 may access the routine 60. The routine 60 may begin at step 62, such as when prompted by step 32 of the method 30, and may proceed to step 64. At step 64 the routine 60 may query the rider as to whether they are in their sweat zone. For example, the rider may receive a message via the input device or devices 20. If the response is no, the method proceeds to step 65 where a timer will run. After timing out at step 65, the method 60 may return to point 68 and then proceed to step 64 and will message the rider again and the method continues. When the rider responds no at step 64, the method also proceeds in parallel to step 67 where the data from sensors 25 is monitored. If a change in state such as an increase in rider cadence or air temperature occurs, then the routine 60 may proceed to step 68, regardless of the state of the timer at step 65, and the rider may again be asked if they are in the sweat zone. If the rider responds yes at step 64, then the routine 60 may proceed to step 70. At step 70 the controller 18 may save a profile in memory, recording information such as the ambient air temperature, the rider's body temperature and current pedaling cadence along with other available sensor data. From step 70 the routine may proceed to step 72 where it is complete and may be triggered again at desirable intervals or events by the method 30. Through the routine 60, the method 30 creates a personalized sweat zone profile for one or a number of unique riders based on external factors. When the sensors 25 encounter the same or similar external factors, the method 30 may trigger an e-assist increase at step 42.

Through the foregoing, a system 10 and method 30 may provide a cycle rider with e-assist to avoid sweating. User input may provide adjustable e-assist intervention levels. The following description of variants is only illustrative of components, elements, acts, products and methods considered to be within the scope of the invention and are not in any way intended to limit such scope by what is specifically disclosed or not expressly set forth. The components, elements, acts, products and methods as described herein may be combined and rearranged other than as expressly described herein and still are considered to be within the scope of the invention.

Variation 1 may involve a method that may include determining whether a sweat sensor is available. E-assist may be provided when a sweat sensor is not available by determining a sweat threshold and determining whether the sweat threshold is surpassed.

Variation 2 may include the method according to variation 1 and may include providing e-assist when a sweat sensor is available by a. determining a sweat threshold and determining whether the sweat threshold is surpassed or b. determining whether the sweat sensor senses sweat.

Variation 3 may include the method according to variation 1 or 2 and may include providing an input device wherein the step of determining the sweat threshold may comprise reading user input from the input device.

Variation 4 may include the method according to variation 3 wherein the step of providing an input device may comprise providing an input device with an incorporated sweat sensor.

Variation 5 may include the method according to any of variations 1 through 4 wherein the sweat threshold may be determined by reading user input and sensed environmental data and looking up the sweat threshold in a table of user input levels and environmental data.

Variation 6 may include the method according to any of variations 1 through 5 wherein when it may be determined that the sweat threshold is surpassed, the method may repeat determining whether the sweat threshold is surpassed, after providing e-assist.

Variation 7 may include the method according to any of variations 1 through 6 and may include providing an input device. The step of determining the sweat threshold may comprise reading user input from the input device.

Variation 8 may include the method according to variation 7 wherein the step of providing an input device may comprise providing a smartphone.

Variation 9 may involve a method of providing e-assist to propel a cycle and may include determining whether a sweat sensor is available. When a sweat sensor is available the method may include at least one of: a. determining a sweat threshold, and determining whether the sweat threshold is surpassed, or b. determining whether the sweat sensor senses sweat.

Variation 10 may include the method according to variation 9, wherein when a sweat sensor is not available, the method may determine a sweat threshold and may determine whether the sweat threshold is surpassed.

Variation 11 may include the method according to variation 10 and may include providing an input device wherein the step of determining the sweat threshold may comprise reading user input from the input device.

Variation 12 may include the method according to variation 11 and may include providing the input device with a selection of various e-assist intervention levels.

Variation 13 may include the method according to variation 11 wherein the step of providing an input device may comprise providing an input device with an incorporated sweat sensor.

Variation 14 may include the method according to variation 9 wherein the sweat threshold may be determined by reading user input and sensed environmental data and looking up the sweat threshold in a table of user input levels and environmental data.

Variation 15 may include the method according to variation 9 wherein when it may be determined that the sweat threshold is surpassed the method may repeat determining whether the sweat threshold is surpassed, after providing e-assist.

Variation 16 may include the method according to variation 9 and may include providing an input device. The step of determining the sweat threshold may comprise reading user input from the input device.

Variation 17 may include the method according to variation 16 and may include providing a wireless interface between the input device and the cycle.

Variation 18 may involve a system providing e-assist to propel a cycle and may include a crank that may propel the cycle with rider effort. A motor may be connected to the cycle and may providing e-assist to propel the cycle. A controller may communicate with the motor, and an input device may provide rider input to the controller.

Variation 19 may include the system of variation 18 wherein the input device may have an incorporated sweat sensor that senses sweat of the rider.

Variation 20 may include the system of variation 18 and may include a sensor communicating with the controller. Environmental data may be provided to the controller and may include at least one of ambient temperature, humidity or wind speed.

The above description of select variations within the scope of the invention is merely illustrative in nature and, thus, variations or variants thereof are not to be regarded as a departure from the spirit and scope of the invention.

What is claimed is:

1. A method for assisting propulsion of a cycle adapted to carry a rider, the method comprising operating a controller configured to:
    determine whether a sweat sensor is available as indicated by whether the sweat sensor is actively communicating with the controller, wherein the sweat sensor is configured to determine whether a first sweat threshold is surpassed by sensing rider sweat;
    when the sweat sensor is not actively communicating with the controller and is therefore not available, determine a second sweat threshold by categorizing, in the controller, user input setting options and an environmental data set for each user input setting option wherein the categorized user input setting options and environmental data sets provide an indication of an exertion level of the rider where a propulsion assistance to the cycle is needed to avoid sweating by the rider as the second sweat threshold;

read a user input device to obtain a selected user input setting selected by the rider;
read a sensor to obtain sensed environmental data indicative of current conditions; and
determine whether the second sweat threshold is surpassed by comparing the selected user input setting and the sensed environmental data to the user input setting options and environmental data sets; and
when the second sweat threshold is surpassed, operate a motor to provide the propulsion assistance to the cycle when the sweat sensor is not available.

2. The method according to claim 1, wherein the sweat sensor is configured to be worn by the rider and senses the presence of moisture, and further comprising providing the propulsion assistance when the sweat sensor is actively communicating with the controller and therefore available by reading, by the controller, the sweat sensor; and determining, by the controller, whether the sweat sensor senses the presence of moisture.

3. The method according to claim 2 further comprising receiving, by the controller, the selected user input setting from the input device that is in communication with the controller, wherein the input device is in the form of an input wristband that is configured to receive the selected user input setting from the rider; and effecting communication between the input device and the controller, wherein the step of determining the second sweat threshold comprises reading, by the controller, the selected user input setting from the input wristband.

4. The method according to claim 3 comprising incorporating the sweat sensor into the input device.

5. The method according to claim 1 wherein determining the second sweat threshold comprises looking up, by the controller, the second sweat threshold in a table stored in the controller and based on the user input setting options and the environmental data sets.

6. The method according to claim 1 wherein when it is determined that the second sweat threshold is surpassed the method further comprises repeating determining whether the second sweat threshold is surpassed after providing the propulsion assistance; and maintaining the propulsion assistance until the selected user input setting and the current environmental data indicate the second sweat threshold is no longer surpassed.

7. The method according to claim 1 wherein the selected user input setting is in the form of a high setting, a medium setting or a low setting.

8. The method according to claim 7 wherein the input device comprises a smartphone.

9. A method of providing an e-assist to propel a cycle configured to have a rider, where the e-assist is a propulsion assistance provided from a motor to the cycle, wherein a controller is configured to carry out the method which comprises:
determining whether a sweat sensor is available wherein the sweat sensor is configured to be worn by the rider, is configured to sense the presence of moisture, and is configured to communicate with the controller, wherein determining whether the sweat sensor is available includes evaluating whether the sweat sensor is actively communicating with the controller;
when the sweat sensor is actively communicating with the controller and therefore available, determining whether the sweat sensor senses the presence of moisture, wherein the presence of moisture indicates a first sweat threshold has been surpassed;
operating the motor to provide the propulsion assistance to the cycle, when the first sweat threshold has been surpassed;
when the sweat sensor is not actively communicating with the controller and is therefore not available, determining a second sweat threshold wherein the sweat threshold is based on measurable environmental data and is indicative of an exertion level of the rider where a propulsion assistance to the cycle is needed to avoid sweating by the rider;
determining whether the second sweat threshold is surpassed; and
when the second sweat threshold is surpassed, operating a motor to provide the propulsion assistance to the cycle, when the sweat sensor is not available.

10. The method according to claim 9 further comprising: when the sweat sensor is not available, reading sensed environmental data from a sensor set and referencing a lookup table that categorizes the measurable environmental data for determining the second sweat threshold; and determining, by the controller, whether the second sweat threshold is surpassed by comparing the sensed environmental data to the measurable environmental data.

11. The method according to claim 10 further comprising: querying the rider, by the controller through an input device, as to whether the rider is sweating; when the rider responds with a negative reply, initiating a timer; when the timer times out, querying the rider again, by the controller through the input device, as to whether the rider is sweating; when the rider responds with a positive reply, saving the sensed environmental data as a profile in a memory of the controller; monitoring, by the controller, the sensor set and when the sensor set indicates the profile of the saved sensed environmental data is again present, providing the e-assist.

12. The method according to claim 11 further comprising providing the input device with a selection of various e-assist intervention levels as a user input setting input by the rider through the input device.

13. The method according to claim 11 comprising incorporating the sweat sensor into the input device.

14. The method according to claim 9 wherein determining whether the second sweat threshold is surpassed, is determined by reading a user input setting and the sensed environmental data and looking up the sweat threshold in a table for the user input setting and sensed environmental data.

15. The method according to claim 9 comprising creating a personalized sweat zone profile of the rider including reading multiple sensors to obtain an ambient air temperature, a body temperature of the rider and a current pedaling cadence of the cycle; and saving the personalized sweat zone profile in a memory of the controller, by recording the ambient air temperature, the body temperature of the rider and the current pedaling cadence of the cycle.

16. The method according to claim 9 further comprising receiving, by the controller, a user input setting from an input device that is in communication with the controller, wherein the input device is in the form of a wristband configured to provide the user input setting; incorporating the sweat sensor into the wristband; and wherein the step of determining the sweat threshold comprises reading, by the controller, the user input setting from the input device and reading, by the controller, a sensor set to obtain the sensed environmental data.

17. The method according to claim 16 further comprising providing a wireless interface between the input device and the cycle.

\* \* \* \* \*